United States Patent [19]

Papahadjopoulos et al.

[11] 4,235,871
[45] Nov. 25, 1980

[54] METHOD OF ENCAPSULATING BIOLOGICALLY ACTIVE MATERIALS IN LIPID VESICLES

[76] Inventors: Demetrios P. Papahadjopoulos, 78 Heathwood, Williamsville, N.Y. 14221; Francis C. Szoka, Jr., 375 Leroy Ave., Buffalo, N.Y. 14214

[21] Appl. No.: 881,116

[22] Filed: Feb. 24, 1978

[51] Int. Cl.$^3$ .................. A61K 9/10; A61K 9/66; A61K 39/02; A61K 37/48
[52] U.S. Cl. ...................... 424/19; 252/316; 424/38; 424/89; 424/92; 424/94; 424/131; 424/177; 424/178; 424/180; 424/248.57; 424/250; 424/330
[58] Field of Search ............ 424/38, 19, 177, 178; 252/316; 260/112.7

[56] References Cited

U.S. PATENT DOCUMENTS

| | | | |
|---|---|---|---|
| 3,804,776 | 4/1974 | Yazawa et al. | 424/38 |
| 4,016,100 | 4/1977 | Suzuki et al. | 252/316 |
| 4,053,585 | 10/1977 | Allison et al. | 424/88 |
| 4,089,801 | 5/1978 | Schneider | 252/316 |

FOREIGN PATENT DOCUMENTS

| | | |
|---|---|---|
| 2249552 | 5/1973 | Fed. Rep. of Germany ........... 252/316 |
| 2532317 | 1/1976 | Fed. Rep. of Germany . |

OTHER PUBLICATIONS

Robinson, Trans. Faraday Soc., 56: 1260-1264 (1960).
Papahadjopoulos et al., Biochim. Biophys. Acta, 135: 639 (1967).
Chowhan et al., Biochim. Biophys. Acta, 266: 320-342 (1972).
Papahadjopoulos et al., Biochim. Biophys. Acta, 135: 624-638 (1967).
Bangham et al., J. Mol. Biol., 13: 238-252 (1965).
Batzri et al., Biochim. Biophys. Acta, 298: 1015 (1973).
Deamer et al., Biochim. Biophys. Acta, 443: 629-634 (1976).
Papahadjopoulos et al., Biochim. Biophys. Acta, 394: 483-491 (1975).
Smith, Chemical Abstracts, 81: 73751c (1974), Rate of cholesterol flip-flop in lipid bilayers and its relation to membrane sterol pools.
G. Colacicco et al., Respiration Physiology (1976), 27, 169-186, North-Holland Publishing Co. Amsterdam.
Trauble and Grell, Neuros. Res. Progr. Bull. 9: 373-380 (1971).
H. Ti Tien et al., Chem. Phys. Lipids 2(1968) 55-101.
A. Darszon et al., J. Cell Biol. 81: 446-452, May 1979.

*Primary Examiner*—Donald G. Daus
*Assistant Examiner*—M. C. Eakin
*Attorney, Agent, or Firm*—Kane, Dalsimer, Kane, Sullivan and Kurucz

[57] ABSTRACT

The disclosure is of a method for encapsulating biologically active materials in synthetic, oligolamellar lipid vesicles (liposomes). The method comprises providing a mixture of lipid in organic solvent and an aqueous mixture of the material for encapsulation, emulsifying the provided mixture, removing the organic solvent and suspending the resultant gel in water. The method of the invention is advantageous over prior art methods of encapsulating biologically active materials in that it provides a means for a relatively high capture efficiency of the material for encapsulation. The disclosure is also of intermediate compositions in the encapsulation method, the product vesicles, compositions including the product vesicles as an active ingredient and their use.

26 Claims, No Drawings

METHOD OF ENCAPSULATING BIOLOGICALLY ACTIVE MATERIALS IN LIPID VESICLES

BACKGROUND OF THE INVENTION

1. Field of the Invention

The invention relates to synthetic lipid vesicles and the method of their manufacture, encapsulating biologically active materials and to their use.

2. Brief Description of the Prior Art

Prior to our invention, several methods have been available to make synthetic liposomes, encapsulating biologically active materials. For example, Robinson, Trans. Faraday Soc., 56:1260–1264 (1960) and Papahadjopoulos et al. (Biochim. Biophys. Acta, 135, 639, 1967) described a method of forming phospholipid dispersions from an ether-lipid-aqueous two-phase system that involved the evaporation of the ether by bubbling nitrogen through the mixture. There was no attempt to use this procedure to entrap organic materials and the trapping efficiency was not investigated in detail. A similar evaporation technique from a chloroformaqueous two-phase system was described by Chowhan et al., in Biochim. Biophys. Acta, 266:320–342 (1972). This procedure also involved the use of excess aqueous phase and the slow removal of the chloroform phase in order to produce a uniform population of phospholipid vesicles. There was no attempt to maximize captured aqueous material and no investigation into the trapping efficiency of this procedure.

Bangham et al. in J. Mol. Biol., 13:238–252 (1965) described multilamellar lipid vesicles which could be characterized as having a small trapping volume, a low trapping efficiency (of 10 percent) and a confined aqueous space (15 to 35 Å).

The small unilamellar vesicles produced by ultrasonication, described initially by D. Papahadjopoulos and N. Miller (Biochim. Biophys. Acta, 135:624–638 [1967]) and by many others since then, have very low capture efficiencies and are unsuitable for encapsulating large macromolecules due to their small aqueous compartment (250 Å).

Lipid vesicles prepared by injection of the lipids in an organic phase into an aqueous solution were described by Batzri and Korn (Biochim. Biophys. Acta, 298:1015 [1973] using ethanol and by Deamer and Bangham in Biochim. Biophys. Acta, 443:629–634 (1976) using ether. These methods produce unilamellar or paucilamellar vesicles but, again do not achieve high efficiencies in encapsulation. In the case of the ethanol injection this low efficiency is due to the large aqueous volume in which the ethanol is dispersed, and the small size of the vesicles produced by the technique. In the case of the ether injection technique, it is due to a combination of the large volume of aqueous space the ether is injected into, the small amounts of lipid employed in the method, and the manner in which the vesicles form.

A preparation of large unilamellar vesicles has been described by Papahadjopoulos et al. in Biochim. Biophys. Acta, 394:483–491 (1975) that involves a unique calcium-induced structural change in the lipid vesicle, but this technique is restricted to a single phospholipid (phosphatidylserine) and also has a relatively low efficiency for encapsulation due to the method of reconstitution of the vesicles.

Another lipid vesicle preparation has been described in German Pat. No. 2,532,317, which involves centrifugation of a lipid-water-ether emulsion into an aqueous phase. The disadvantage of this technique is that high speed centrifugation is required and a large amount of the lipid-aqueous emulsion becomes trapped at the interface and does not enter the aqueous phase. This reduces the percentage of material entrapment.

The U.S. Pat. No. 3,804,776 is noteworthy for its disclosure of a method for producing oil and fat encapsulated amino acids or polypeptides by dispersing powders of the desired material for encapsulation in a molten mixture of the fat or oil and thereafter pouring the molten mixture into water. The encapsulated material is contained within relatively large droplets of lipid which restricts their use to oral administration to an animal. The method is somewhat restrictive to that it apparently is limited to encapsulation of powders, and the lipid does not form a bilayer.

Finally, mention may be made of U.S. Pat. No. 4,016,100 which describes the entrapment of certain pharmaceuticals in lipid vesicles by freezing the aqueous phospholipid dispersion of pharmaceutical and lipid. The pharmaceutical compounds disclosed for encapsulation by the reference method generally exhibit a high partition coefficient into an organic phase from water. Therefore it would be expected that the material for encapsulation would penetrate into the phospholipid bilayers of the product vesicles. Theoretically this would provide a high degree of encapsulation but there remains an open question as to the bio-availability of the total material encapsulated. It would also be expected that relatively high rates of encapsulation would not be obtained if the technique were applied to encapsulate pharmaceuticals which are of a more polar nature and less likely to penetrate the vesicle bilayers.

By the method of our invention, oligolamellar lipid vesicles (synthetic liposomes) may be constructed rapidly, conveniently, under mild conditions, in high yields, and in such a manner that they incorporate a high percentage of a wide variety of biologically active material processed with them. Representative of material which may be encapsulated by the method of the invention are pharmaceutically active compounds and compositions thereof, carbohydrates, nucleotides, polynucleotides (both naturally occurring and synthetic) pesticides, including fungicides, insecticides, miticides, nematocides and mollusicides, water soluble fertilizers and agricultural nutrients, peptides, proteins, enzymes, viruses and the like. Many of these materials do not normally penetrate the plasma membrane of cells and may be inactivated in circulation within a living organism or by contact with tissue and organ cultures. In the case of pesticides and agricultural nutrients or fertilizers they may be removed from the area of application by rain or irrigation. Encapsulation of such materials protects them from inactivation or removal, i.e.; maintains bioavailability. Bacterial cells such as *C. parvum* and *E. coli* and the like may also be encapsulated by the method of the invention for protection and bioavailability.

The method of the invention may also be used to encapsulate cosmetic preparations which may be usefully employed as described in U.S. Pat. No. 3,957,971.

SUMMARY OF THE INVENTION

The invention comprises a method of encapsulating biologically active materials in synthetic, oligolamellar lipid vesicles, which comprises;

providing a mixture of a vesicle wall forming compound in organic solvent and an aqueous mixture of the biologically active material to be encapsulated, the ratio of organic phase to aqueous phase being that which will produce an emulsion of the water-in-oil type;

forming a homogeneous emulsion of said mixture, of the character produced by ultra-sonic radiation;

removing organic solvent from the emulsion, whereby a mixture is obtained having a gel-like character; and converting the gel-like mixture to synthetic, oligolamellar vesicles encapsulating the biologically active material.

The invention also comprises the intermediate gel-like material, the product synthetic lipid vesicles, their use and carrier compositions including the synthetic vesicles as the active ingredient thereof.

The term "biologically active material" as used throughout the specification and claims means a compound or composition which, when present in an effective amount, reacts with and/or affects living cells and organisms.

The term "synthetic, oligolamellar lipid vesicles (liposomes)" as used herein means man-made lipid vesicles, created in the laboratory and characterized in part by few or single bimolecular lipid layers forming the vesicle walls.

The method of the invention is useful to make synthetic, oligolamellar or unilamellar lipid vesicles which in turn are usefully employed in a wide variety of processes. For example, the lipid vesicles prepared by the method of the invention may be used to enhance the bioavailability of medications, to enhance enzyme replacement, oral drug delivery, topical drug delivery, for introducing genetic information into cells in vitro and in vivo, for the production of vaccines, for the introduction of recombinant deoxyribonucleic acid segments into microbial cells, or as diagnostic reagents for clinical tests following release of entrapped "reporter" molecules. The lipid vesicles produced by the method of the invention may also be employed to encapsulate cosmetic preparations, pesticides, compounds for sustained slow release to effect the growth of plants and the like.

DETAILED DESCRIPTION OF THE PREFERRED EMBODIMENTS OF THE INVENTION

In a broad sense, the method of the invention calls for the formation first of "inverted micelles" in an organic phase and then the removal of the organic phase. The system then spontaneously reverts to a bilayer-like structure, with a large amount of aqueous phase encapsulated in large oligolamellar vesicles. The advantage of this method is that it gives high capture efficiencies of aqueous phase and provides large, stable vesicles. Phospholipids are excellent molecules for the formation of the "inverted micelles" and then the subsequent bilayer of the vesicles. More specifically, the method of the invention is carried out as follows.

The first step in the method of the invention is to provide a mixture of a lipid vesicle wall forming composition in organic solvent and an aqueous mixture of the biologically active material to be encapsulated in the vesicle. Vesicle wall forming compounds are generally well known as are the methods of their preparation. For example, any number of phospholipids or lipid compounds may be used to form the vesicle walls. Representative of such wall forming compounds are; phosphatidylcholine (hereinafter referred to as "PC"), both naturally occurring and synthetically prepared, phosphatidic acid (hereinafter referred to as "PA"), lysophosphatidylcholine, phosphatidylserine (hereinafter referred to as "PS"), phosphatidylethanolamine (hereinafter referred to as "PE"), sphingolipids, phosphatidylglycerol (hereinafter referred to as "PG"), spingomyelin, cardiolipin, glycolipids, gangliosides, cerebrosides and the like used either singularly or intermixed such as in soybean phospholipids (Asolectin, Associated Concentrates). In addition, other lipids such as steroids, cholesterol, aliphatic amines such as long chain aliphatic amines and carboxylic acids, long chain sulfates and phosphates, dicetyl phosphate, butylated hydroxytoluene, tocophenol, retinol, and isoprenoid compounds may be intermixed with the phospholipid components to confer certain desired and known properties on the formed vesicles. In addition, synthetic phospholipids containing either altered aliphatic portions such as hydroxyl groups, branched carbon chains, cycloderivatives, aromatic derivatives, ethers, amides, polyunsaturated derivatives, halogenated derivatives or altered hydrophillic portions containing carbohydrate, glycol, phosphate, phosphonate, quaternary amine, sulfate, sulfonate, carboxy, amine, sulfhydryl, imidazole groups and combinations of such groups can be either substituted or intermixed with the above mentioned phospholipids and used in the process of the invention. It will be appreciated from the above that the chemical composition of the lipid component of the vesicles prepared by the method of the invention may be varied greatly without appreciable diminution of percentage capture although the size of the vesicle may be affected by the lipid composition. A convenient mixture we have used extensively and which is representative of lipid mixtures advantageously used in the method of the invention is composed of PS and PC, or PG and PC as identified above (advantageously at a 1:4 molar ratio in each instance). The PC, PG, PA and PE, may be derived from purified egg yolk. Saturated synthetic PC and PG, such as dipalmitoyl may also be used. Other amphipathic lipids that may be used, advantageously also at 1:4 molar ratios with PC, are gangliosides, globosides, fatty acids, stearylamine, long chain alcohols, and the like.

The liposome wall forming composition may be initially provided dissolved in any inert solvent that can be substantially removed from the lipid of phospholipid compound when desired. Representative of such solvents are a wide variety of ethers, esters, alcohols, ketones, hydrocarbons (aromatic and aliphatic including fluorocarbons), and silicones in which an aqueous phase does not have an appreciable solubility. The solvents may be used either alone or in admixture. For each solvent or mixture of solvents however, the optimal ratio of lipid, aqueous space, and solvent is different and must be determined for each case by trial and error techniques as will be appreciated by those skilled in the art. The term "inert solvent" as used herein means a solvent for the lipid or phospholipid, which will not interfere with or otherwise adversely affect the desired course of the method of the invention.

The phospholipid or lipid along with any lipid-soluble additives, are advantageously evaporated from their solvent on to the sides of a suitable reaction vessel. The organic phase, in which the "reversed phase evaporation vesicles" of the invention will be formed is then added to the vessel, i.e., an inert organic solvent for the lipids and phospholipids as described above. With mixing, dissolution of the lipid component of the vesicles to be formed, previously deposited on the vessel walls is obtained. A number of inert organic solvents are preferred for forming the organic phase according to the method of the invention, depending on the following conditions of the method employed. For low temperature conditions, i.e.; removal subsequently of the organic phase at relatively low temperatures, we find diethyl ether most advantageous, although chloroform, or tetrahydrofuran may also be used advantageously. For higher temperature processing, isopropyl ether is a preferred inert organic solvent, particularly for preparing lipid vesicles containing saturated phospholipids as the lipid component. Following dissolution of the phospholipid or lipid to form the organic phase, an aqueous phase is added to obtain a heterogeneous 2-phase mixture. The aqueous phase contains in dissolution/suspension the compounds or compositions to be encapsulated in the synthetic lipid vesicles produced by the method of the invention. Preferably the aqueous phase is buffered to a pH suitable to maintain stability of the material for encapsulation. The ionic strength of the aqueous phase has a bearing on the encapsulation efficiency obtained in the method of the invention. As a general rule, the higher the ionic strength of the aqueous phase, the lower the percentage of entrapment. For example, with 15 mM sodium chloride present, one can encapsulate circa 60 percent of the aqueous phase, while with 500 mM sodium chloride present, only about 20 percent of the aqueous phase may be encapsulated. Thus, to maximize the encapsulation of macromolecules, a buffer of low ionic strength (less than 0.3) is preferably employed. The encapsulation efficiency is also dependent to some degree on the concentration of lipid or phospholipid present in the 2-phase system. Preferably the proportion of lipid or phospholipid component is within the range of from about 0.5 mg to about 50 mg/ml. of the inert organic solvent. Preferably the ratio of organic phase to aqueous phase is within the range of from about 2:1 to about 20:1 v/v, most preferably about 4:1 to form a water-in-oil emulsion.

The heterogeneous 2-phase mixture obtained as described above is then emulsified to obtain an emulsion of the character produced by ultrasonic radiation. Preferably this is accomplished with the use of a bath type sonicator, or for large volume preparations in an industrial size emulsifier. Generally, the 2-phase mixture is sonicated for about 3 to 5 minutes, or until either a clear 1-phase mixture or a homogeneous emulsion forms. This is achieved by simply placing the container vessel in the sonicating bath at an optimal level. Emulsification may be carried out over a wide range of temperatures, i.e.; from about −10° to about 50° C., advantageously at a temperature of from 0°-20° C. The optimum conditions under which emulsification is carried out depends upon the solvent, phospholipid, and volume of aqueous phase used in the preparation. It will be appreciated that trial and error techniques may be used to determine the optimum conditions for emulsification. The emulsion mixture is then treated to remove a substantial portion of the inert organic solvent. This may be carried out conveniently by use of a rotary evaporator, at a temperature of circa 20° C. to 60° C. and under a reduced pressure, i.e.; under vacuum (10 mm to 50 mm Hg). The temperature employed for evaporation of the organic solvent from the emulsion depends on the boiling point of the particular organic solvent used in the emulsion and the stability of the biologically active material being encapsulated. During evaporation, the emulsion first becomes a viscous gel, which is an intermediate product. The gel is stable and can be stored in this state for short periods of time, up to a week (at least), at 4° C. under an inert atmosphere such as nitrogen gas. A small amount of water or buffer can then be added to the gel and the resulting mixture evaporated for an additional period (circa 15 minutes) to help remove residual traces of the organic solvent, and to speed the conversion of the gel into a homogeneous-appearing, suspension of oligolamellar lipid vesicles. The gel may be converted by agitation or by dispersion in an aqueous media such as a buffer solution. The vesicles obtained range in diameter from 2,000 to 4,000 angstroms (average). A significant proportion of the drugs, chemicals, macromolecules, or other compounds and biological materials for encapsulation contained in the aqueous buffer is captured within the lipid vesicles (up to circa 60 percent, depending on the amount of lipid, volume of the aqueous phase, ratio of the organic phase to aqueous phase to lipid, type of inert organic solvent(s) and, type of lipid(s) used in the process). The non-incorporated aqueous material may be removed if necessary by appropriate and known techniques such as by repeated centrifugations, column chromatography, ion exchange chromatography, dialysis and like procedures. The lipid vesicles with their encapsulated contents can then be suspended in any isotonic buffer for use. The vesicles may be sterilized by passage through a 0.4 micron filter (nucleopore) when sterility is desired.

Representative of materials and compounds that may be encapsulated by the method of the invention include but are not limited to drugs such as cytosine arabinoside, and its phosphorylated derivatives; chemicals such as cyclic 3', 5' adenosine monophosphate, sucrose, antibiotics such as penicillin and streptomycin, polypeptide hormones such as insulin, oxytocin, and vasopressin, macromolecules such as dextran, proteins such as albumin, ferritin, and immunoglobulin G; enzymes such as alkaline phosphatase; nucleic acids such as polyadenylic acid (poly A), ribonucleic acids, deoxyribonucleic acids, virus and bacteria such as *C. parvum* and like materials.

Advantageously the method of the invention is carried out under an inert atmosphere. The term "inert atmosphere" as used herein means a non-oxidizing atmosphere such as an atmosphere of nitrogen gas, argon and like inert gases.

It will be observed from the above that the method of our invention differs from the prior art methods in several ways. For example, according to our method the material to be encapsulated is added into the organic phase with the lipid where it is totally encapsulated. Furthermore, the organic phase is substantially removed before an excess of an aqueous phase is added. The emulsification of the initial aqueous phase into the organic phase, and the removal of the organic phase prior to the addition of any excess aqueous phase is essential for high capture percentage in this method and is a critical difference between the process of our invention and all previous methods heretofore described. The method of the invention produces large oligolamellar vesicles from many different lipids either alone or in combinations. An advantage of the method of the invention is that the evaporation of the organic phase is performed under mild temperatures and vacuum to obviate the potential for inactivation of sensitive molecules.

The following examples describe the manner and process of making and using the invention and represent the best mode contemplated by the inventors, but are not to be construed as limiting. In all of the procedures described below, one can include 0.5 to 1 mole of a fluorescent phospholipid analog such as NBD-PE (Avanti Biochemicals) with the lipid or phospholipid component in order to be able to visually follow the separation of the vesicles on a column.

EXAMPLE 1 Encapsulation of Enzymes

A 50 ml round bottom flask with a long extension neck is fitted with a 24/40 fitting so as to conveniently couple to a flash evaporator. The flask is also fitted for continuous purging with nitrogen gas. The flask is charged with 10μ moles of phosphatidylglycerol, 40μ moles of phosphatidylcholine and 50μ moles of cholesterol dissolved in chloroform. With rotary evaporation, the solvent is evaporated leaving a thin lipid layer on the inner walls of the flask. The flask is then purged with nitrogen gas and 5 ml of diethyl ether added with stirring to dissolve the lipids. Then 1.5 ml of an aqueous mixture of 10 mM sodium chloride buffered to a pH of 7.4 with 4 mM of histidine/2-{[tris (hydroxymethyl) methyl] amino} ethanesulfonic acid (hereinafter referred to as "TES") and 10 mg/ml of alkaline phosphatase is added to the flask to form a heterogeneous, 2-phase mixture. The mixture is then emulsified by sonication for 5 minutes at 0° C. in a bath-type ultrasonic cleaner (model T-80-80-IRS, Laboratory Supplies, Hicksville, New York). The resulting emulsion is then evaporated on a rotary evaporator (Buchi) at a temperature of 25° C. and under a reduced pressure (circa 10–50 mm Hg) using a water aspirator until a viscous gel results. This gel is an intermediate precursor of the synthetic liposomes to be prepared. The gel is stable and may be stored for periods of at least one week at a temperature of circa 4° C. under an inert atmosphere.

To the gel obtained above there is added 1.5 ml. of the sodium chloride/histidine/TES buffer described above and the flask is rotated gently to obtain an aqueous suspension of the gel. The resulting mixture is evaporated at 30° C. under a pressure of circa 10–50 mm Hg for an additional 15 minutes to obtain an opaque suspension of phospholipid vesicles (synthetic liposomes) having mean diameters of 0.2 to 0.6 microns. Prolonged evaporation without addition of extra buffer will result in similar suspensions. Examination under an electron microscope shows the vesicles to be substantially oligolamellar vesicles.

The opaque suspension of vesicles is passed through a Bio-gel A 1.5 agarose column to separate the oligolamellar vesicles from unencapsulated alkaline phosphatase mixture. The percent of encapsulation is calculated to be 34 percent. The separated vesicles may be suspended in any isotonic buffer and used as the starting material for an enzyme reagent.

Similarly, repeating the above procedure for Example 1 but replacing the alkaline phosphatase as used therein with 10 mg/ml of L-asparaginase, synthetic vesicles are obtained encapsulating the L-asparaginase. The vesicles are useful in inhibiting certain tumor growths in mammals; see Chang, T., Nature 229, 117–118 (1971) for the technique of use.

Similarly, repeating the above procedure of Example 1, but replacing the alkaline phosphatase as used therein with 10 mg/ml of various glycosidases, synthetic vesicles are obtained encapsulating the enzymes. The product vesicles are useful in enzyme replacement therapy; see "Enzyme Therapy in Lysosomal Storage Diseases", Tager, Hooghwinkel and Daems; North-Hullang Publ. Co., (1974) for the technique of use.

Similarly, repeating the above procedure of Example 1 but replacing the alkaline phosphatase as used therein with 84 mg/ml of 1-β-D-arabinofuranosylcytosine, synthetic vesicles are obtained encapsulating the arabinofuranosylcytosine for use in inhibiting certain tumor growths in mammals; see Mayhew et al., Cancer Research, 36: 4406–4411, December 1976 for the technique of use. In like manner, nucleoside analogues of ara-C, methotrexate or like antimetabolites may be encapsulated for use in inhibiting certain tumor growths in mammals.

Similarly, repeating the above procedure of Example 1 but replacing the alkaline phosphatase as used therein with 0.6 mg/ml of actinomycin D, this compound is encapsulated. Actinomycin D encapsulated by the above described procedure may be administered to patients suffering from responsive cancers, following the method of Gregoriadis et al., Lancet, June 29, 1974, pages 1313–1316; see also D. Papahadjopoulos, et al., *Cancer Research*, 36: 2988–2994, September 1976.

Similarly, repeating the above procedure of Example 1 but replacing the phosphatase as used therein with the sodium salt of heparin dissolved in phosphate buffered saline, synthetic vesicles are obtained encapsulating heparin. The vesicles may be suspended in buffer solution and administered intraveneously to a mammal as a sustained release anticoagulant, to treat responsive afflictions. Similarly drugs such as meglumine antimoniate can be encapsulated by the same procedure of Example 1. Meglumine antimoniate encapsulated by the above described procedure can be used in mammals against parasitic organisms such as Leishmaniasis. Similarly, repeating the above procedure of Example 1 but replacing the phosphatase as used therein with metal chelating compounds such as ethylenediaminetetraacetic acid (EDTA), penicillamine, and the like, synthetic vesicles are obtained that can be used in treating patients suffering from metal poisonings, metal storage problems, or certain anemias; see U.S. Pat. No. 4,016,290.

EXAMPLE 2 Encapsulation of Nucleic Acids

The round-bottom flask described in Example 1, supra. is charged with 10μ moles of phosphatidylglycerol, 40μ moles of phosphatidylcholine and 50μ moles of cholesterol dissolved in chloroform. The charge is evaporated on a rotary evaporator to deposit a thin lipid layer on the inner walls of the flask. The flask is purged with nitrogen gas and 5 ml of diethyl ether added to the flask with stirring to redissolve the lipids. Then 1.5 ml. of an aqueous mixture of 10 mM sodium chloride buffered to a pH of 7.4 with 4 mM of histidine/TES and 1 mg/ml of ribonucleic acid (RNA) (either polyadenylic acid or 25S tetrahymena ribosomal RNA). The resulting mixture is emulsified by sonication for 5 minutes at a temperature of 0° C. in the bath-type ultrasonic cleaner (Laboratory Supplies, supra). The emulsion is then evaporated at a temperature of 0° C. and under a pressure of 10–50 mm Hg on the flash evaporator until a gel is formed. To the gel there is added 1.5 ml of the sodium chloride/histidine/TES buffer solution described above and evaporation is continued for an additional 15 minutes. The resulting opaque suspension is of synthetic vesicles encapsulating the ribonucleic acid.

After standing at a temperature of 20° C. for about 30 minutes, the suspension is centrifuged at 100,000 X G for 30 minutes. The supernatent is then removed, leaving as sediment the synthetic, encapsulating vesicles. The percentage of RNA encapsulation is calculated to be 40 to 43 percent. The vesicles are useful for inserting the RNA through cellular membranes.

Similarly, repeating the above procedure of Example 2, but replacing the ribonucleic acid as used therein with the insect virus nucleopolyhedrosis and 1 mg per ml para-aminobenzoic acid, synthetic vesicles are obtained encapsulating this virus for use as a pesticide. The vesicle encapsulated pesticide may be used to control a number of insect pests as detailed in chapter 29 *Viruses and Invertebrates*, A. J. Gibbs Ed., North Holland Publishing Company, by spraying an effective amount of the encapsulated pesticide, in a water mixture, on sites of infestation or potential sites of infestation. Methods of determining effective amounts for a given pest are well known; see for example U.S. Pat. Nos. 3,474,170; 3,476,836; and 3,478,029. The applied vesicles will remain effective for controlling the organism over extended periods of time.

Similarly, other polyribonucleotides such as polyinosinic-poly-cytosinic acid, or other synthetic polynucleotides can be substituted for the ribonucleic acid in the procedure of Example 2 to form synthetic lipid visicles, encapsulating these compounds for use as anti-viral agents. The techniques of using such vesicles are well known.

Similarly, repeating the above procedure but replacing the ribonucleic acid as used therein with deoxyribonucleic acid, synthetic vesicles are obtained encapsulating the deoxyribonucleic acid. The product vesicles may be used as a means to transfer genetic information to either encaryotic or bacterial cells.

EXAMPLE 3 Encapsulation of Insulin

The round-bottom flask described in Example 1, supra., is charged with 50μ moles of dipalmitoyl phosphatidylcholine and 50μ moles of cholesterol in chloroform. The charge is evaporated on a rotary evaporator to deposit the lipid mixture on the inner walls of the flask. The flask is then purged with nitrogen gas and 7.5 ml of isopropyl ether and 7.5 ml of chloroform added with stirring to redissolve the lipids. To the solution there is added 1.5 ml of an aqueous mixture of insulin (bovine, 20 mg/ml in 7 M urea) in aqueous buffer (10 mM triethylamine hydrochloride; pH 7.9). The resulting mixture is then emulsified by sonication for 5 minutes at a temperature of 45° C. in a sonicator bath (Laboratory Supplies, supra.). The emulsion is then evaporated at a temperature of 45° C. and under a pressure of 10–50 mm Hg. on a flask evaporator until a gel is formed. To the gel there is added 1.5 ml of the sodium chloride/TES buffer previously described, with stirring. Evaporation is then continued for an additional 15 minutes. The resulting opaque suspension is allowed to stand for 30 minutes at a temperature of 45° C. The suspension is then passed through a G-75 Sephadex column at room temperature (circa 26° C.) to separate synthetic lipid vesicles, encapsulating the insulin solution. The percentage of insulin encapsulation is calculated to be 34 percent. The vesicles may be suspended in phosphate buffered saline and administered orally or intramuscularly at conventional dosage levels to patients suffering from insulin controlled diabetes. The above procedure can be repeated at lower temperatures during sonication and evaporation (0°–20° C.) if fluid phospholipids are used for the formation of vesicles instead of dipalmitoylphosphatidylcholine.

Similarly, repeating the above procedure but replacing the insulin with other water-soluble peptide hormones, such as vasopresin, somatostatin or their synthetic derivatives and analogues, synthetic lipid vesicles are obtained encapsulating such material, for use in therapeutic applications to mammals suffering responsive diseases.

EXAMPLE 4 Encapsulation of Sulfoxone

The round-bottom flask described in Example 1, supra., is charged with 50μ moles of soybean lecithin (Asolectin, Associated Concentrates, Woodside, New York) and 50μ moles β-sitosterol in chloroform. The mixture is evaporated on a rotary evaporator to deposit the lipid mixture of the inner walls of the flask. The flask is then purged with nitrogen gas and 5 ml of diethylether is added with stirring to redissolve the lipids. To the solution is added 1.5 ml of an aqueous mixture of sulfoxone sodium, (disodium [sulfonylbis (p-phenylenimino)] dimethanesulfinate) 25 mg/ml, and sodium ascorbate 5 mg/ml. The resulting mixture is emulsified by sonication for 5 minutes at a temperature of 0° C. in a sonicator, (Laboratory Supplies, supra). The emulsion is then evaporated at a temperature of 20° C. and under a pressure of 10–50 mm Hg on a flash evaporator until a gel is formed. To the gel there is added 1.5 ml of a 10 mM ammonium chloride solution with stirring. Evaporation is continued for an additional 15 minutes. The encapsulated sulfoxone is separated from unencapsulated sulfoxone solution by dialysis. The vesicles so obtained may then be used as an antibacterial preparation for applications to plants, by suspending them in buffer solution and spraying the solution over the root zones of the plant in an effective amount to act as an antibacterial.

Similarly, repeating the above procedure but replacing the sulfoxone sodium and sodium ascorbate with 50 mg/ml streptomycin sulfate, synthetic lipid vesicles are obtained encapsulating such material, for use as an antibacterial preparation for applications to plants.

As mentioned above, the ionic strength of the aqueous mixture for encapsulation is a determining factor for the degree of encapsulation obtained in the method of the invention. As the ionic strength of the aqueous mixture for encapsulation increases, there is a decrease in both the percentage of encapsulation and in the volume of encapsulated aqueous space per $\mu$ mole of phospholipid. High concentrations of sucrose glycerol, urea and the like do not have the same effect as increasing the concentration of ionic species in the mixture for encapsulation. This effect is shown in the following Example 5.

EXAMPLE 5

The procedure of Example 1, supra. is repeated six times, but in each case the alkaline phosphatase as used in Example 1 is replaced with 0.84 mg/ml of 1-β-D-arabinofuranosylcytosine (ara-C) and the proportion of sodium chloride in each repetition is varied to vary the ionic strength of the ara-C mixture for encapsulation. The proportion of sodium chloride present and the resulting degree of encapsulation obtained are shown in Table 1, below.

TABLE I

| Run No. | Moles NaCl | Percentage Encapsulation |
|---|---|---|
| 1 | 0.50 | 15.0 |
| 2 | 0.15 | 37.5 |
| 3 | 0.10 | 42.5 |
| 4 | 0.04 | 47.5 |
| 5 | 0.02 | 62.3 |
| 6 | 0.00 | 62.5 |

The lipid concentration in the two phase mixture for emulsification also has a bearing on the percentage of encapsulation obtained by the method of the invention. For example, the percentage of ara-C encapsulation decreases with decreasing total lipid concentrations. However, the aqueous volume encapsulated per mole of phospholipid increases.

An aqueous volume of about 11.2 liters per mole of phospholipid is encapsulated when the lipid totals about 100$\mu$ moles per 5 ml solvent and increases to about 22.5 liters per mole of phospholipid when the total lipid is reduced to 20$\mu$ moles. The range of 20–100 $\mu$M/5 ml is preferred, above 100 $\mu$M producing increased numbers of multi-lamellar vesicles. Example 6 below illustrates the percentage of ara-C encapsulation obtained under various lipid concentrations.

EXAMPLE 6

The procedure of Example 1, supra, is repeated five times, but in each case the alkaline phosphatase as used therein is replaced with 84 mg/ml of 1-$\beta$-D-arabinofuranosylcytosine (ara-C) and the total lipid concentration is varied for each repetition (while maintaining the same ratio of PG:PC:cholesterol). The total proportion of lipid used in each repetition and the percent of encapsulation obtained is shown in Table 2, below.

TABLE 2

| Run No. | Total Lipid ($\mu$ Moles) | Percent of Encapsulation |
|---|---|---|
| 1 | 20 | 15 |
| 2 | 40 | 25 |
| 3 | 60 | 30 |
| 4 | 80 | 31.2 |
| 5 | 100 | 37.5 |

The nature of the lipid or lipids employed in the method of the invention does not appear to be critical. With the exception of negatively charged lipids when used alone such as PS, PG, cardiolipin or phosphatidic acid, different lipid compositions at similar proportions of lipid/solvent/buffer have only a moderate effect on the degree of encapsulation obtained. Example 7, below, illustrates this conclusion.

EXAMPLE 7

The procedure of Example 1, supra, is repeated several times, except that the alkaline phosphatase as used therein is replaced with 0.84 mg/ml of ara-C or 0.01 M of sodium chloride in 1/10 Dulbecco's phosphate buffered saline instead of TES and in each repetition the lipid component is varied. In Run No. 4, 3.5 ml. of diethyl ether and 1.05 ml of the Dulbecco's saline (PBS) was used; in Run No. 5, 7.5 ml. of isopropyl ether with 7.5 ml. of chloroform was used in place of the diethyl ether and the second evaporation was conducted at 45° C.; in Run No. 6, a mixture of 7.5 ml. isopropyl ether and 7.5 ml. ethanol was used in place of the diethyl ether; in Runs No. 7 and 8, a mixture of 5 ml. of diethyl ether with 1 ml. of methanol was used in place of the diethyl ether alone. The lipids used, the lipid concentration employed and the percentage of encapsulation achieved in each case is shown in Table 3, below.

TABLE 3

| Run No. | Lipid Composition | Total Lipid ($\mu$ Moles) | Percent ara-C | Encapsulation sodium |
|---|---|---|---|---|
| 1 | PG/PC/Chol* (1:4:5) | 100 | 62 | 47.5 |
| 2 | PG/PC (1:4) | 50 | — | 34.3 |
| 3 | PS/PC/Chol (1:4:5) | 100 | 61 | — |
| 4 | Stam**/PC/Chol (1:4:3) | 56 | — | 44.6 |
| 5 | DPPC | 50 | — | 40.6 |
| 6 | Sphingomyelin | 66 | 24 | — |
| 7 | PG | 50 | — | 18.6 |
| 8 | PS | 50 | — | 22 |

*Chol represents cholesterol
**Stam represents stearylamine

The vesicles prepared by the method of the invention function as carriers for the encapsulated, biologically active material which remains bioavailable. The vesicle walls are impermeable to the encapsulated materials as shown in Example 8.

EXAMPLE 8

Three 10 ml. portions of the vesicles prepared in Example 5, run No. 5 were separated and dialyzed overnight to remove unencapsulated material present in the suspension of ara-C encapsulated vesicles. Each dialyzed portion was then placed in a dialysis bag and dialyzed against three consecutive 10 ml. portions of Dulbecco's phosphate buffered saline for 1 hour each at various temperatures. The percentage of ara-C diffusing through the dialysis bag per hour was then observed. The observations, temperatures employed and length of dialysis are shown in Table 4, below.

TABLE 4

| | Percentage of entrapped material released per hour. | | |
|---|---|---|---|
| | Temperature °C. | | |
| Time | 10 | 20 | 37 |
| 1 Hour | .376 | .697 | 1.97 |
| 2 Hours | .221 | .613 | 1.69 |
| 3 Hours | .195 | .649 | 1.54 |

EXAMPLE 9 ENCAPSULATION OF BACTERIA

The round bottom flask described in Example 1, supra. is charged with 50 $\mu$moles PG:PC (1:4) and 50 moles cholesterol dissolved in chloroform. With rotary evaporation, the solvent is evaporated leaving a film of the lipid mixture on the inner walls of the flask. The flask is then purged with nitrogen gas and 5 ml of diethylether is added with stirring to redissolve the lipids. To the solution is added 1.5 ml of an aqueous suspension of the heat-killed bacterium *C. parvum* in Dulbecco's phosphate buffered saline*. The resulting mixture is emulsified by sonification for 5 minutes at 0° C. in a sonicator, (Laboratory supplies, supra.). The emulsion is then evaporated at a temperature of 20° C. and under a reduced pressure of 10–50 mm Hg on a flash evaporator until a gel is formed. To the gel is added 1.5 ml of Dulbecco's phosphate buffered saline and the evaporation is continued for an additional 15 minutes. The encapsulated *C. parvum* is separated from unencapsulated *C. parvum* by centrifugation on a sucrose gradient. Thirty percent of the presented *C. parvum* is encapsulated. The vesicles so obtained may be used as an adjuvant for immunotherapy against certain cancers as detailed in Seminars Oncol. 1:367–378, 1974.

*Dulbecco's phosphate buffered saline (NaCl, 0.137 M; NaHPO$_4$, 8.2×10$^{-3}$ M; KCl, 2.7×10$^{-3}$ M; KH$_2$PO$_4$, 1.9×10$^{-3}$ M; MgCl$_2$, 1.1×10$^{-3}$ M; CaCl$_2$, 0.9×10$^{-3}$ M).

Similarly repeating the above procedure for Example 9 but replacing the C. parvum as used therein with other immunostimulants such as BCG, intact cancerous cells, or purification fractions of these, synthetic vesicles are obtained encapsulating such material. These vesicles would be useful in immunotherapy when administered to a mammal suffering from a responsive affliction.

The Example 9 also demonstrates a particular advantage of the method of the invention in that it provides a means of not only encapsulating materials in solution, but materials in suspension in an aqueous media as well. The material for encapsulation may be dissolved in the aqueous phase if soluble. Alternatively, the material may be finely divided and suspended in the aqueous medium or it may be macromolecules in suspension such as in the case of virus or cellular materials. It appears that if there is room for the suspended material within the product vesicle, it can be encapsulated by the method of the invention. This is an advantage of the method of the invention since many of the prior art methods of encapsulation will not be feasible for the encapsulation of other than dissolved materials.

The product vesicles prepared by the method of the invention have been demonstrated to encapsulate large volumes and relatively large materials having biological activity. Depending on the nature of the encapsulated materials, the vesicles have a very broad range of utility. For example, with encapsulated antibiotics they may be used in-vivo and in-vitro to treat antibiotic resistant pathogens, including the gram-negative E. coli, H. influenzae, P. aeruginosa and the like. The theory has been expressed that drug resistance developed by bacterial organisms is a result of developing impermeability of the cell wall. Delivery of an appropriate antibiotic to the organism is facilitated when effected through a lipid vesicle means since the lipid vesicle seems to readily penetrate the bacterial cell wall, releasing the encapsulated antibiotic within the pathogen.

Similarly, as briefly described above, by encapsulation of anti-parasite compounds, one can deliver the encapsulated material to the reticuloendothelial system of a host mammal. The lipid vesicle can deliver the medication efficiently to neutralize the parasite with minimal toxic effect on the host mammal.

The encapsulation of viral and bacterial agents such as inactivated polio virus or P. aeruginosa provides a vaccine which may be administered to a mammal to give that mammal immunization against disease caused by the agent, with a reduction of toxicity potential associated with such vaccines which are not encapsulated by the method of the invention.

The method of the invention may be used to encapsulate deoxyribonucleic acid (DNA) described above. Encapsulated DNA fragments can be inserted into living cells, both plant and animal through the delivery vehicle of the lipid vesicle. The advantage is in labor and time saving over present methods which comprise the plasmid and splicing techniques. The vesicle encapsulated DNA is protected from degradation by enzymes.

What is claimed is:

1. A method of encapsulating biologically active materials in synthetic, oligolamellar, lipid vesicles, which comprises:
    providing a mixture of a vesicle wall forming compound in organic solvent and an aqueous mixture of the biologically active material to be encapsulated, the ratio of organic phase to aqueous phase being that which will produce an emulsion of the water-in-oil type;
    forming a homogeneous water-in-oil type of emulsion of said mixture;
    evaporating organic solvent from the emulsion, until a mixture is obtained having a gel-like character; and
    converting the gel-like mixture to a suspension of synthetic, oligolamellar vesicles encapsulating the biologically active material by one of the steps of (a) agitating said gel-like mixture and (b) dispersing said gel-like mixture in an aqueous media.

2. The method of claim 1 wherein the wall forming compound is a phospholipid.

3. The method of claim 2 wherein the phospholipid comprises phosphatidylcholine in admixture with a second phospholipid and cholesterol.

4. The method of claim 3 wherein the proportion of phosphatidylcholine is in a ratio of 4:1 to the second phospholipid.

5. The method of claim 1 wherein the wall forming compound is initially provided in an inert solvent and is then deposited on the side wall of a reaction vessel by evaporation of the inert solvent.

6. The method of claim 1 wherein the organic solvent is selected from the group consisting of diethyl ether, chloroform, tetrahydrofuran and isopropyl ether.

7. The method of claim 1 wherein the aqueous mixture is buffered to a pH suitable to maintain stability of the biologically active material.

8. The method of claim 7 wherein the buffer is an ionic compound, at a strength of less than 0.3 units.

9. The method of claim 1 wherein the proportion of wall forming compound is within the range of from about 0.5 mg to about 50 mg per milliliter of the organic solvent.

10. The method of claim 1 wherein emulsification is carried out with ultrasonic radiation at a temperature of from about $-10°$ to about $50°$ C.

11. The method of claim 1 carried out under an inert atmosphere.

12. The method of claim 1 wherein the aqueous mixture comprises water buffered to a pH suitable to maintain stability of the biologically active material.

13. The method of claim 1 wherein the oligolamellar vesicles are then separated from unencapsulated biologically active materials.

14. The method of claim 1 wherein the biologically active material is an enzyme.

15. The method of claim 1 wherein the biologically active material is an antibiotic.

16. The method of claim 1 wherein the biologically active material is a nucleic acid.

17. The method of claim 16 wherein the nucleic acid is a deoxyribonucleic acid.

18. The method of claim 1 wherein the biologically active material is a pesticide.

19. The method of claim 1 wherein the biologically active material is a polypeptide.

20. The method of claim 19 wherein the polypeptide is insulin.

21. The method of claim 1 wherein the biologically active material is a bacterial organism.

22. The method of claim 1 wherein the biologically active material is a virus.

23. The method of claim 1 wherein the wall forming compound is a mixture of cholesterol, phosphatidyl-glycerol and phosphatidylcholine in a ratio of 5:1:4 by weight.

24. The product of the process of claim 1.

25. The method of claim 1 wherein the ratio of organic phase to aqueous phase is within the range of from about 2:1 to about 20:1 v/v.

26. The method of claim 25 wherein said ratio is 4:1.